US009820820B2

(12) United States Patent
Jess et al.

(10) Patent No.: US 9,820,820 B2
(45) Date of Patent: Nov. 21, 2017

(54) MODULE FOR A VISUALIZATION APPARATUS FOR VIEWING AN OBJECT

(71) Applicant: Carl Zeiss Meditec AG, Jena (DE)

(72) Inventors: Helge Jess, Oberkochen (DE); Michael Wirth, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 196 days.

(21) Appl. No.: 14/609,285

(22) Filed: Jan. 29, 2015

(65) Prior Publication Data

US 2015/0209116 A1 Jul. 30, 2015

(30) Foreign Application Priority Data

Jan. 29, 2014 (DE) .......................... 10 2014 201 571

(51) Int. Cl.
| | |
|---|---|
| *G02B 21/00* | (2006.01) |
| *A61B 19/00* | (2006.01) |
| *G02B 21/36* | (2006.01) |
| *G02B 21/22* | (2006.01) |
| *A61B 90/20* | (2016.01) |

(52) U.S. Cl.
CPC .......... *A61B 19/5223* (2013.01); *A61B 90/20* (2016.02); *G02B 21/0012* (2013.01); *G02B 21/22* (2013.01); *G02B 21/361* (2013.01)

(58) Field of Classification Search
CPC .............................................. A61B 19/5223; A61B 90/20; G02B 21/0012; G02B 21/22; G02B 21/361
See application file for complete search history.

(56) References Cited

U.S. PATENT DOCUMENTS

| | | | | |
|---|---|---|---|---|
| 2006/0250684 | A1* | 11/2006 | Sander | G02B 21/0012 359/368 |
| 2009/0279052 | A1* | 11/2009 | Hauger | A61B 3/13 351/208 |
| 2012/0033064 | A1* | 2/2012 | Yamada | G02B 21/0004 348/79 |

FOREIGN PATENT DOCUMENTS

| | | |
|---|---|---|
| DE | 101 57 613 A1 | 10/2002 |
| WO | 2009/080790 A1 | 7/2009 |
| WO | 2009/080791 A1 | 7/2009 |
| WO | 2013/072422 A1 | 5/2013 |

OTHER PUBLICATIONS

English translation and the Office action of the German Patent Office dated May 20, 2014 in German patent application 10 2014 201 571.5 on which the claim of priority is based.

* cited by examiner

*Primary Examiner* — Francis M Legasse, Jr.
(74) *Attorney, Agent, or Firm* — Walter Ottesen, P.A.

(57) ABSTRACT

A module for a visualization apparatus includes an imaging optic accommodated in a base body for generating a viewing image of an object region with an optical viewing beam path. The module includes a display unit for visualizing an image superimposed on the viewed image of the object region with orientation information. The module has an image acquisition unit having an image sensor for acquiring an image of the object region. The module contains a switching unit for selectively providing and blocking an optical beam path from the display to the image sensor. The switching unit, in a first switching state, provides the image of a geometric structure on the display onto the image sensor with the optical beam path and, in a further switching state blocks the optical beam path from a geometric structure on the display to the image sensor.

23 Claims, 12 Drawing Sheets

MODULE FOR A VISUALIZATION APPARATUS FOR VIEWING AN OBJECT

CROSS REFERENCE TO RELATED APPLICATION

This application claims priority of German patent application no. 10 2014 201 571.5, filed Jan. 29, 2014, the entire content of which is incorporated herein by reference.

FIELD OF THE INVENTION

The invention relates to a module for a visualization apparatus comprising an imaging optical unit accommodated in a basic body for generating an observation image of an object region, with an optical viewing beam path, comprising a display device having a display for visualizing an image superimposed on the observation image of the object region, the superimposed image having orientation information, and comprising an image acquisition device having an image sensor for acquiring an image of the object region.

BACKGROUND OF THE INVENTION

Within the meaning of the invention, orientation information is understood to mean in particular auxiliary geometries which are superimposed on an observation image in surgical microscopes. With such auxiliary geometries it is possible, for example, to facilitate orientation in an operating area for an operator. For example, with such auxiliary geometries, tissue and bone structures in an operating area can be indicated precisely to an operator. Orientation information within the meaning of the invention can, however, also consist in images which are recorded preoperatively on a patient using diagnostic apparatuses such as MRT (Magnetic Resonance Tomography) or MRI (Magnetic Resonance Imaging) apparatuses, for example, and which show the structures in an operating area which cannot be identified or can only be identified with difficulty by an observer in the observation image of an object region.

In this case, a module is understood to mean both an assembly which is permanently integrated in a visualization apparatus and an assembly which is designed for replaceable supplementation or retrofitting of a visualization device and which can be connected to a basic body of a visualization device, for example using dovetail couplings.

A visualization apparatus comprising a module of the type mentioned at the outset is known from WO 2013/072422 A1. The document describes a visualization apparatus in the form of a surgical microscope which has an imaging optical unit which generates an observation image of an object plane. This surgical microscope is an eye surgery microscopy system. It contains an electronic image sensor, which is connected to a computer unit for calculating the position and orientation of a patient's eye by means of image analysis. Thus, orientation information in the form of a calculated auxiliary geometry which is superimposed, in correlated form, on the observation image of a patient's eye can be displayed to an observer.

In order to enable precise orientation within an operating area for an operator, it is necessary for the superimposed orientation information displayed to be aligned precisely with respect to the observation image in such a visualization apparatus.

The computer unit of the visualization apparatus described in WO 2013/072422 A1 contains a computer program for this purpose, which computer program enables compensation for determined errors during acquisition of the image data on which the digitally generated images are based and matching of image data to determined position, orientation and scaling errors.

DE 101 57 613 A1 discloses a visualization apparatus in which the image of a display can be provided both in the optical channel of an optical observation beam path and on an image sensor for acquiring an object region image in the corresponding observation beam path. In the case of the display of display information in the observation beam path by means of the display, the display information is in this case always supplied to the image sensor.

SUMMARY OF THE INVENTION

It is an object of the invention to provide a visualization apparatus which allows simple and precise adjustment of orientation information which is superimposed on a viewing image, and to provide a method with which a systematic error in orientation information can be determined precisely in a visualization apparatus in order to enable the display of orientation information without this systematic error.

The visualization apparatus of the invention is for viewing an object. The visualization apparatus includes: a base body; an imaging optic mounted in the base body and defining an optical viewing beam path; the imaging optic being configured for generating a viewing image of a region of the object via the optical viewing beam path; a module including: a display unit having a display and being configured for visualizing an image superposed on the viewing image of the object region; the superposed image having orientation information in the optical viewing beam path; an optical channel for the optical viewing beam path; an image acquisition unit having an image sensor for detecting an image of the region of the object; an in-coupling beam splitter arranged in the optical channel; the display and the image sensor conjointly defining an optical beam path running from the display to the image sensor and passing through the beam splitter; a switching unit for selectively passing and blocking the optical beam path; the in-coupling beam splitter being configured to deflect the optical beam path from the display into the optical channel so as to be superposed on the optical viewing beam path; and, the switching unit having a first switching state wherein an image of a geometric structure shown on the display is made available on the image sensor via the optical beam path and having a second switching state, which is different from the first switching state, wherein the optical beam path is blocked to prevent the geometric structure shown on the display from reaching the image sensor.

The inventors have identified that the display of an image which is superimposed on the viewed image of an object region in a visualization apparatus often has systematic errors which can only be compensated for by adjustment of optical assemblies with a great deal of complexity. These systematic errors can be noticeable in particular when orientation information with which the position of structures and areas in an object region is specified, for example the contours of a tumor or the position or orientation of a patient's eye, is intended to be superimposed on the observation image in a visualization apparatus. That is, that, in this case, it is desirable for this orientation information to in any case be subject to a residual error which is so minor that it does not impair, that is, reduce, the accuracy of surgical interventions or diagnoses which are possible for a patient with such a visualization apparatus.

One concept of the invention therefore comprises a display device with which a calculated image which is superimposed on the image of an object region can be visualized preferably being adjusted computationally automatically in a visualization apparatus by virtue of the systematic errors of an image displayed by a display, whose cause firstly lies in the connection and/or manufacturing and/or installation and adjustment tolerances of the display and secondly in the connection and/or manufacturing and/or installation and adjustment tolerances of the image acquisition device or of the image sensor arranged therein or else in manufacturing and adjustment tolerances of the imaging lens systems for the display and the image acquisition device, being taken into consideration in the calculation of the image data for the display device. Therefore, not only the manufacturing complexity for such a visualization apparatus can be reduced. The compensation of systematic errors of an image displayed in such a visualization apparatus using a computer unit furthermore also introduces an accuracy for the display of orientation information which is calculated by means of image analysis of image data acquired by a replaceable camera in a surgical microscope which cannot be achieved at all using the methods of a conventional mechanical adjustment of assemblies.

The geometric structure in a module according to the invention comprises, where possible, a pattern which defines the position and at least one length and the azimuthal orientation of the display content of the display.

In a visualization apparatus designed for the field of neurosurgery, for example, this orientation information can consist in the contours of a tumor in an operating area or in vessels which extend in an operating area. In a visualization apparatus designed for the field of ophthalmology, the orientation information in question can be the circle of the capsulorhexis, the position of toric lenses, the main axes of an astigmatism or a run of stitching in the case of cornea transplantation.

A module according to the invention preferably has an optical channel for the optical viewing beam path in which a coupling-out beam splitter is arranged in order to supply the observation image of the object region to the image acquisition device. Then, a coupling-in beam splitter is located in the optical channel in order to superimpose an image displayed on the display of the display device on the observation image of the object region in the viewing beam path.

The switchable device can have in particular a beam deflection system which deflects an optical beam path coming from the display and passing through the coupling-in beam splitter and then supplies the optical beam path to the image sensor via the coupling-out beam splitter, for optional provision and suppression of an optical beam path from the display to the image sensor.

Preferably, the beam deflection system is designed in such a way that it directs the optical beam path coming from the display on a side of the coupling-in beam splitter which is remote from the display, by reflection on a first mirror surface, to a second mirror surface, which reflects the optical beam path to a side of the coupling-out beam splitter which is remote from the image acquisition device.

According to a feature of the invention, the beam deflection system can contain, for example, a 90° prism for deflecting the optical beam path coming from the display.

In the case of a module according to the invention, furthermore an optical element for optionally enabling and interrupting the beam path passing through the coupling-in beam splitter can also be provided between the coupling-in beam splitter and the coupling-out beam splitter. This optical element is preferably in the form of a shutter, which can be moved into the beam path and out of the beam path. Particularly preferably, this shutter is in the form of a relocatable light trap, which receives the light impinging on the shutter from the object region and the display when the module is integrated in a surgical microscope.

The coupling-in beam splitter and the coupling-out beam splitter can each have a splitter surface with a splitter layer. Then, it is in particular also possible for the switchable device to contain a beam deflection system which has a relocatable mirror, which reflects the optical beam path superimposed on the optical viewing beam path by means of the coupling-in beam splitter by deflection at the splitter surface thereof back from the display into the coupling-in beam splitter and supplies the superimposed optical beam path to the coupling-out beam splitter through the splitter surface of the coupling-in beam splitter. In the coupling-out beam splitter, this optical beam path can then in turn be reflected on the splitter surface thereof to a further deflection mirror arranged on a side of the coupling-out beam splitter which is remote from the image acquisition device in order to then supply the optical beam path through the coupling-out beam splitter with a beam path passing through the splitter surface thereof to the image acquisition device.

As switchable device for optionally providing and suppressing an optical beam path from the display to the image sensor, a relocation device can also be provided, which serves the purpose of moving the coupling-in beam splitter and the coupling-out beam splitter out of a first position into a second position, and vice versa. The coupling-out beam splitter in this case, in the first position, supplies the observation image of the object region to the image acquisition device, and the coupling-out beam splitter superimposes an image displayed on the display of the display device on the observation image of the object region in the viewing beam path. In the second position, the coupling-in beam splitter directs an image displayed on the display of the display device to the coupling-out beam splitter which, in the second position, supplies this image to the image acquisition device.

As an alternative to this, it is also possible for the coupling-in beam splitter and the coupling-out beam splitter to be combined in the module so as to form a common beam splitter and for the display device for visualizing an image superimposed on the observation image of the object region to be formed with polarized light, wherein a switchable optical element is arranged in the beam path supplied to the image acquisition device between the beam splitter and the image sensor, which switchable optical element is transmissive to the polarized light of the display device in a first switching state and, in a further switching state, which is different than the first switching state, suppresses the passage of the polarized light from the display device to the image sensor.

The module can also contain a geometric structure which is spaced apart from the display and is arranged fixed in position relative to the basic body and can have a switchable device for optionally providing and suppressing an image of the geometric structure on the image sensor. This switchable device then provides, in a first switching state, the image of the geometric structure on the image sensor with an optical beam path and, in a further switching state, which is different than the first switching state, suppresses the optical beam path from the geometric structure to the image sensor.

In this case too, a coupling-out beam splitter can be arranged in an optical channel for the optical viewing beam path in order to supply an observation image of an object region to the image acquisition device. In particular also a coupling-in beam splitter can be located in this optical channel in order to superimpose an image displayed on the display of the display device on the observation image of the object region in the viewing beam path.

As switchable device for the optional provision and suppression of an image of the geometric structure on the image sensor, for example, an illumination device for illuminating the geometric structure is advantageous.

The optical channel in a module according to the invention can be, for example, an optical channel for a first stereoscopic component viewing beam path in a visualization apparatus. A module according to the invention can also have a further optical channel for a second stereoscopic component viewing beam path in a visualization apparatus. It is advantageous if an optical element for the at least partial compensation of the optical path length for the first stereoscopic component viewing beam path in the optical channel and of the optical path length for the second stereoscopic component viewing beam path in the further optical channel is provided in this further optical channel.

It is advantageous also to arrange an optical element in the additional further optical channel, which optical element is used for at least partially compensating for the light intensity of the first stereoscopic component viewing beam path in the optical channel and the light intensity of the second stereoscopic component viewing beam path in the further optical channel. A module according to the invention can also contain an optical element which can be arranged in the optical viewing beam path on that side of the coupling-out beam splitter which faces an object region for optionally enabling and interrupting the beam path supplied to the coupling-out beam splitter from the object region.

The invention also extends to a visualization apparatus, in particular a surgical microscope, comprising an imaging optical unit accommodated in a basic body for generating an observation image of an object region which contains a correspondingly designed module.

Furthermore, the invention also extends to a method for matching data displayed in such a visualization apparatus by the display device to the image of an object region acquired by the image acquisition device, in which the image of the geometric structure is provided to the image acquisition device, and in which then correction parameters are determined from the position and/or the size and/or the orientation of the geometric structure in the image of the geometric structure acquired by the image acquisition device on the image sensor in order to compensate for in particular a discrepancy, caused by tolerances of assemblies, in the position and/or the orientation and/or the scaling of an image acquired in the image acquisition device on the image sensor in a system of coordinates which is fixed with respect to the display of the display device for the data which can be displayed by the display device.

In order to implement this method, it is advantageous if the visualization apparatus contains a computer unit, which is connected to the image acquisition device and the display device, having a computer program which can implement the method specified above.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
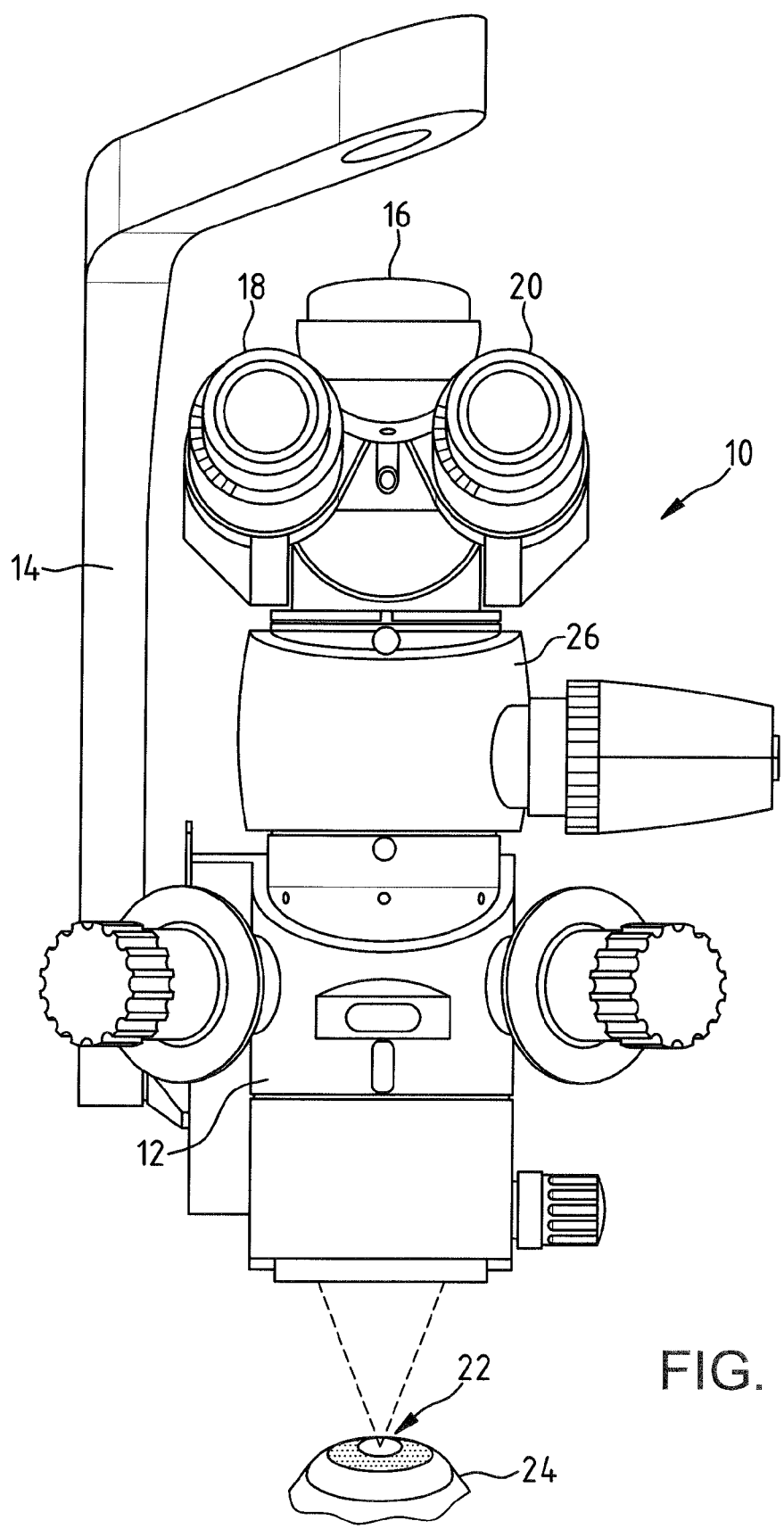
FIG. 1 shows a visualization apparatus in the form of a surgical microscope including a module for mirroring in data displayed by a display device.

The stereoscopic surgical microscope 10 shown in FIG. 1 is for use in ophthalmology (ophthalmological surgical microscope). The surgical microscope 10 has a basic body 12, which is accommodated on a supporting arm 14 of a surgical microscope stand (not illustrated in any more detail) and contains a binocular tube 16 with a left-hand and a right-hand binocular viewer (18, 20), through which an observer can observe, in enlarged form, an object region 22 with an optical viewing beam path.

The surgical microscope 10 is particularly well suited to the performance of cataract surgical procedures in which the natural lens in the eye 24 of a patient is replaced by an artificial intraocular lens.

In order to facilitate the orientation in the object region for an observer and in order to display additional information for the observer when viewing into the binocular tube 16, which additional information is superimposed on the observation image of the object region 22, the surgical microscope 10 contains an optical assembly configured as a replaceable module 26 for data mirroring including a display device and an image acquisition device.

It should be noted that the module 26 can, however, also in principle be in the form of a non replaceable assembly which is fixedly integrated in the basic body of a surgical microscope.

Figure 2:
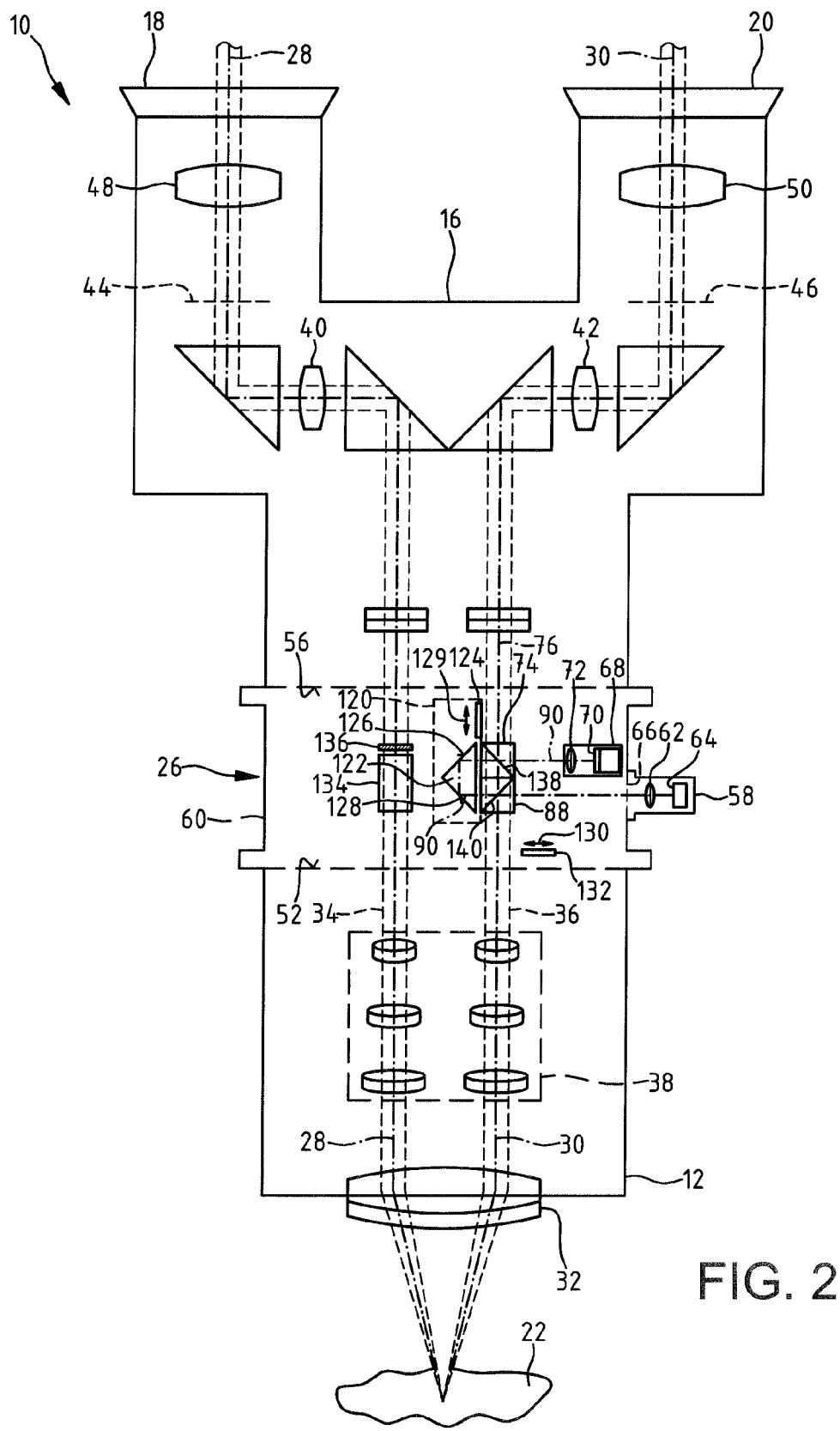
FIG. 2 shows a first and a second stereoscopic component viewing beam path in the visualization apparatus including an image acquisition device and including a display device of the module.

FIG. 2 shows the first and a second stereoscopic component viewing beam path (30, 28) in the surgical microscope 10. The stereoscopic component viewing beam paths (28, 30) are guided in a left-hand and a right-hand optical channel (34, 36) in the surgical microscope 10. They pass through a common microscope main objective 32 and pass through an afocal magnification system 38 with adjustable magnifications. The stereoscopic component viewing beam paths (28, 30) are guided through the module 26 along parallel beam paths. They are focused in the binocular tube 16 with the tube lenses (40, 42) of the left-hand or right-hand intermediate image plane (44, 46), which can be observed in enlarged form by an observer with observer eyes adapted to infinity through a left-hand and right-hand ocular lens system (48, 50).

In the module 26, the image displayed on a display 70 can be superimposed on the image of the object region 22 which can be perceived in the right-hand binocular viewer 20 of the binocular tube 16 in the stereoscopic component viewing beam path 30 in the right-hand optical channel 36.

The module 26 has a module basic body 60 and has a first optomechanical interface 52, at which it is connected to the surgical microscope basic body 12 by a dovetail coupling. Furthermore, the module 26 includes a second optomechanical interface 56 for the binocular tube 16 of the surgical microscope 10. The binocular tube 16 and the module 26 are also in this case in turn connected by a dovetail coupling.

As image acquisition device 58, there is a video camera connected to the module basic body 60 comprising an objective lens system 62 and an image sensor 64 in the module 26. In order to fix and release the image acquisition device 58, a further interface 66 is formed on the module basic body 60.

It should be noted that the module 26 in a modified embodiment can, in principle, also contain an image acquisition device which is fixedly integrated in the module basic body 60.

The image of the object region 22 of the surgical microscope 10 is supplied to the image acquisition device 58 via a coupling-out beam splitter 88, which is arranged in the right-hand optical channel 36 in the module 26.

It is possible with the display device 68 in the module 26 to display orientation information referenced to the observation image of the object region 22 for an observer in the binocular viewer 20 of the binocular tube 16. The display device 68 contains, for this purpose, a display 70 and comprises an imaging lens system 72, by means of which the image information displayed on the display 70 is transferred to a parallel beam path 90 in order to direct the image information into the binocular tube 16 via a coupling-in beam splitter 74 arranged in the module 26 with an optical display beam path 76 superimposed on the stereoscopic component viewing beam path 30.

A computer unit having a data storage medium (not shown) is assigned to the surgical microscope 10 for controlling the image acquisition device 58 and the display device 68. The computer unit contains a computer program, which makes it possible to subject an image acquired by the image acquisition device 58 to image analysis in order to thus acquire the position and the orientation of structures of an object arranged in the object region 22 of the surgical microscope in order to display this information or information derived therefrom to an observer with the display device 68.

Figure 3:
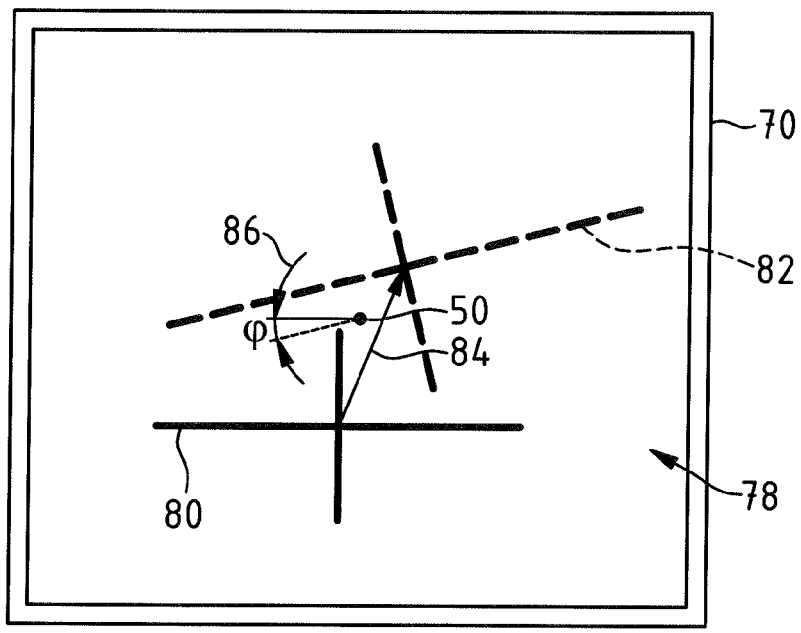
FIG. 3 shows the display of the module with a displayed geometric structure.

FIG. 3 shows the display 70 with an image 78, which is displayed on the display 70. The image 78 contains orientation information 80. In this case, the orientation information 80 is an auxiliary geometry for displaying a position in the object region and/or for displaying an orientation in the object region, such as, for example, the azimuthal orientation of a toric intraocular lens. The position, orientation and scaling or the imaging scale of this orientation information 80 displayed in the binocular tube have not been corrected here.

Once the correction parameters have been determined, in this case the corrected orientation information 82 is inserted as information derived from the position and orientation of structures in the object region. The arrow 84, the angle 86 and the change (exaggerated for illustrative purposes) to the scaling of the corrected and uncorrected orientation information in FIG. 3 illustrate the corrections by the computer unit. These corrections are necessary in order that an operator can move, for example, a toric intraocular lens into the correct orientation on the basis of orientation information 82 calculated and referenced with respect to the eye of a patient by means of the computer unit by image analysis or that a displayed structure can be represented correctly as to position, orientation and size for other applications.

In order to ensure that the orientation information 82 displayed to an observer by the display 70 of the display device 68 is referenced with respect to the image of the object region 22 perceived by the observer in a manner which is correct in terms of location, position and size, the image sensor field of view visualized by the observer needs to correspond to the position, orientation and scaling in the display image.

Figure 4A:
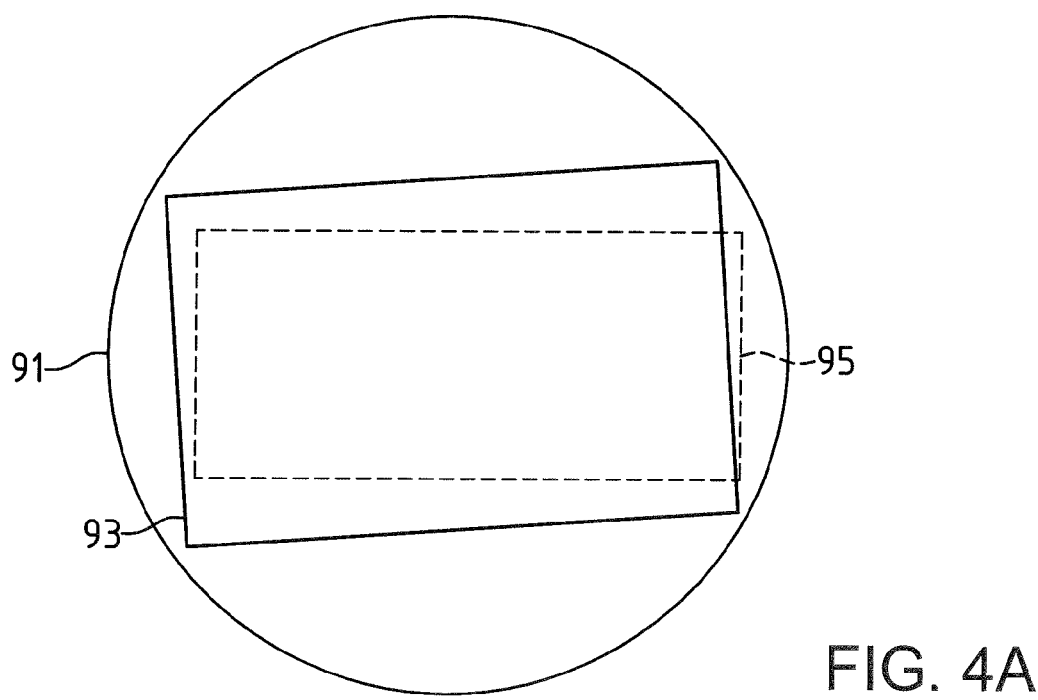
FIG. 4A shows an image sensor and display field of view perceived by an observer in the visualization apparatus prior to matching of the data displayed by the display device to an object region image acquired by the image acquisition device.

FIG. 4A shows an image 91 to be observed by an observer in the binocular viewer 20 of the surgical microscope 10 with an image sensor field of view 93 of the image acquisition device 58 and a display image 95 of the display device 68. With reference to the image sensor field of view 93, the display image 95 is generally shifted in terms of position and orientation owing to fitting and manufacturing tolerances, and the display image can have a size which deviates from the image sensor field of view 93, which is known but generally deviates from the setpoint value owing to tolerances.

Figure 4B:
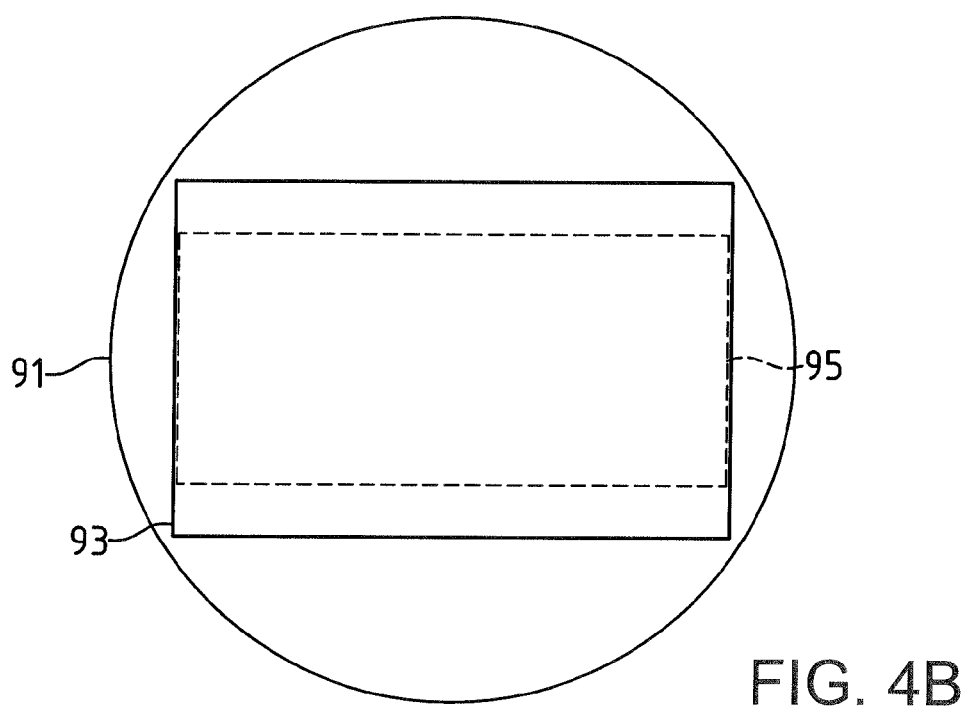
FIG. 4B shows the image sensor and display field of view perceived by an observer in the visualization apparatus after matching of the data displayed by the display device to an object region image acquired by the image acquisition device.

FIG. 4B shows the image sensor field of view 93 and display image 95 acquired by the observer in the binocular viewer on the basis of matching by correction of systematic errors of the image sensor field of view and display image (93, 95) which can be perceived with the display device and image acquisition device. The image sensor field of view 93 and the structures in the display image 95 correspond to one another with respect to position, orientation and scaling, that is, in terms of the imaging scale.

The desired matching of the display image 95 to the image sensor field of view 93 can be ensured in the surgical microscope 10 in principle by a mechanical adjustment of the imaging lens system 72 and of the position of the display 70 in the display device 68 and by a mechanical adjustment of the optical assembly of the image acquisition device 58. However, such a mechanical adjustment is time-consuming and very susceptible to faults. This can therefore generally not be implemented by conventional users of a surgical microscope. Such an adjustment is in principle necessary from scratch whenever the image acquisition device 58 or optical assemblies in the display device 68 are replaced in the case of a module with open interfaces, however.

In order that, in the case of open interfaces in the surgical microscope 10, such a mechanical adjustment can be dispensed with and in order to ensure the accuracy of the matching of the display image to the image sensor field of view over the entire service life of the surgical microscope 10, an optical beam path 90 from the display 70 of the display device 68 to the image sensor 64 of the image acquisition device 58 can be optionally provided or suppressed in the module 26.

By virtue of such an optical beam path 90 being provided, it is possible to display a geometric structure by means of the display 70 of the display device 68, which geometric structure is supplied to the image sensor 64 of the image acquisition device 58. This enables the computational determination of correction parameters, on the basis of which an image of the object region 22 acquired by the image acquisition device 58 can be displayed for an observer in the binocular viewer 20 of the surgical microscope 10 in such a way that the observation image of the object region 22 which can be perceived by the observer and the image of the object region 22 acquired by the image acquisition device and displayed by the display device 60 are congruent for the observer in the region displayed by the display device 60.

Figure 5:
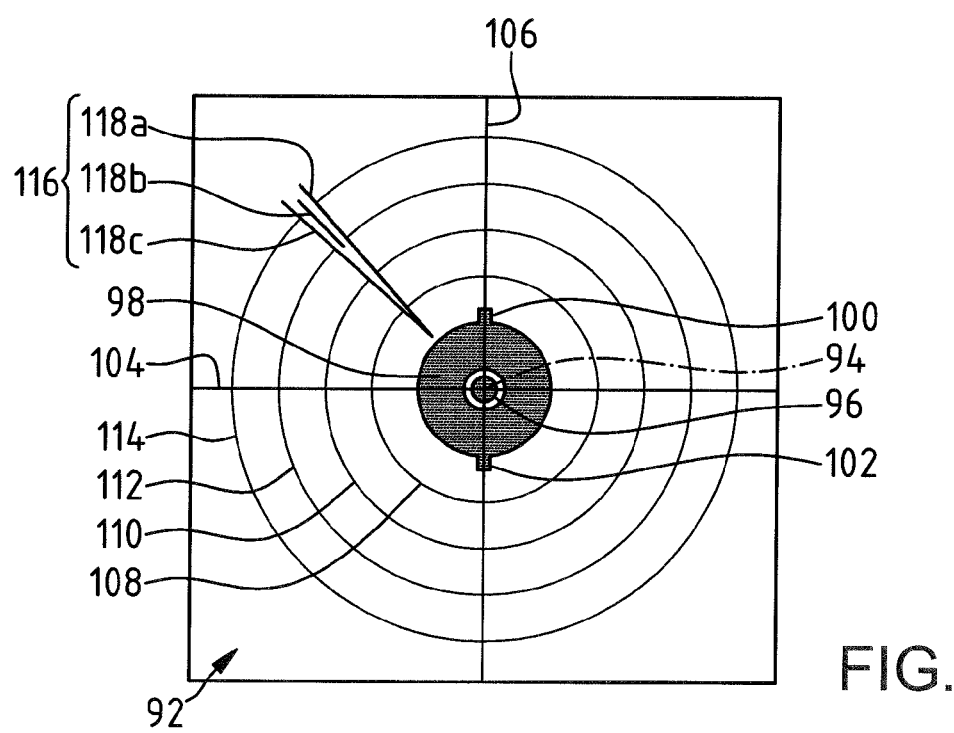
FIG. 5 shows a geometric structure displayed on the display for matching the display device to the image acquisition device.

An example of such a geometric structure is shown in FIG. 5. The geometric structure 92 in FIG. 5 has the form of a target with a center 94. The geometric structure 92 comprises a circular disk 96 arranged concentrically with respect to the center 94, which circular disk is located in a geometric structure in the form of a circular ring 98 arranged concentrically with respect thereto. Two bar shaped markings (100, 102) which are opposite one another are provided on the outer circumference of the circular ring 98. The geometric structure 92 contains two lines (104, 106) which are arranged perpendicular to one another and which have a point of intersection which coincides with the center 94. The two markings (100, 102) are located on the line 106. The geometric structure 92 also has four circular lines 108, 110, 112 and 114 which are concentric with respect to one another and which are arranged concentrically around the circular ring 98. The geometric structure 92 additionally contains an azimuthal angle marking 116 with three angle line marks (118*a*, 118*b*, 118*c*) arranged successively at an angular spacing of 1°.

On the basis of the lines (104, 106) and the circular lines 108, 110, 112 and 114, the pattern of the geometric structure 92 makes it possible to determine the position of the structure 92, the length thereof, that is, the imaging scale, and the azimuthal orientation thereof in a system of coordinates which is fixed with respect to the image sensor 64 of the image acquisition device 58.

In order to optionally provide or suppress the optical beam path 90 from the display 70 of the display device 60 to the image sensor 64 of the image acquisition device 58 in the module 26 of the surgical microscope 10, the module 26 contains a switchable device 120 comprising a 90° prism 122 acting as beam deflection system and a displaceable shutter 124, which acts as light trap. The prism 122 directs that part of the beam path 90 of the display 70 which is not mirrored by the coupling-in beam splitter 74 into the stereoscopic component viewing beam path 30, by reflection on a first mirror surface 126 and on a second mirror surface 128, to the side of the coupling-out beam splitter 88 which is remote from the image acquisition device 58. The displaceable shutter 124 can be moved into the optical beam path 90 in the direction indicated by the double arrow 129 between the coupling-in beam splitter 74 and the 90° prism in order to optionally enable or interrupt this beam path. If the shutter 124 blocks the beam path 90, it acts as a light trap which absorbs the light impinging on the shutter 124 owing to a light absorbing surface property.

In order to match the display device 68 in the surgical microscope 10 to the image acquisition device 58, first the image of the geometric structure 92 (FIG. 5) is provided by the image acquisition device 58 in the surgical microscope 10.

Then, an imaging specification is determined in the computer unit from the position and/or the size and/or the orientation of the geometric structure 92 or of another suitable structure in the image of the geometric structure acquired by the image acquisition device 58 on the image sensor 64.

In order to determine the desired imaging specification, the computer unit first, for example, correlates the image of the geometric structure 92 acquired by means of the image sensor 64 with ring shaped comparison objects of different sizes. This is described in detail on page 3, line 12 to page 4, line 14, and page 5, line 9, to page 9, line 15, of the international patent application with the reference PCT/EP2008/068104 (designating the United States) and also in the international patent application with the reference PCT/EP2008/068103 (designating the United States), both incorporated herein by reference.

Thus, the center 94 of the geometric structure 92 and the outer radius $r_1$ of the circular ring 98 are determined. When the center 94 and the outer radius of the circular ring 98 have been determined, the image acquired by the image sensor 64 is transformed into polar coordinates, and then the azimuthal position of the markings (100, 102) is correlated, by correlation, with two surface elements acting as azimuthal angle markings, the angular spacing W of the surface elements being W =180° in polar coordinates, which surface elements extend over a radius range of $r_1 < r < r_2$, where $r_1$ corresponds to the outer radius of the circular ring 98, and $r_2 := 1.2 r_1$ corresponds to the radius $r_2$ of a further circular ring laid around the circular ring 98, which further circular ring is concentric with respect to the circular ring 98.

The correlation is in this case performed by calculation of a correlation function, for example while varying the location, with the result that the correlation function is a function of the location variables. In this case, the values of the pixels of the image are set against the values of the pixels of the comparison object while the comparison object is moved over the image acquired by the image acquisition device 58. The value of the correlation function is a measure of the correspondence between the image and the comparison object. In the case of maximum correspondence between the image and the comparison object, that is, when the characteristic feature of the comparison object and the sought characteristic feature in the image lie on top of one another, the value of the correlation function is at a maximum, for example.

On the basis of the imaging specification thus determined, the data which can be displayed by the display device 68 are then corrected by means of the computer unit in order to thus in particular compensate for a discrepancy, brought about by tolerances of assemblies, in the position and/or the orientation and/or the scaling of an image acquired in the image acquisition device 58 on the image sensor 64 in a system of coordinates which is fixed with respect to the display 70 of the display device 68.

In order that the image sensor 64 in the image acquisition device 58 only receives the light of the display in the display device 68 when a geometric structure 92 is displayed there in order to match the display device 68 to the image acquisition device 58, an optical element 132 which is arranged relocatably corresponding to the double arrow 130 is provided in the module 26 for optionally enabling and interrupting the second stereoscopic component viewing beam path 30 supplied from the object region 22.

In order to ensure an identical optical path length and an identical image brightness in the surgical microscope 10 for the first and second stereoscopic component viewing beam paths (28, 30), a glass cube 134 through which the first stereoscopic component viewing beam path passes is arranged in the left-hand optical channel 34 and a gray filter 136 is positioned there, which matches the brightness of the light in the optical channel 34 to the loss in intensity of the light in the optical channel 36 which is caused by the splitter surface 138 in the coupling-in beam splitter 74 and the splitter surface 140 in the coupling-out beam splitter 88.

It should be noted that a module according to the invention can in principle also be implemented without the possibility of the mechanical adjustment of the imaging lens system 72 and of the position of the display 70 in the display device 68 and without the possibility of the mechanical adjustment of the optical assembly of the image acquisition device 58. In a module according to the invention, there is always the possibility of technical matching of the data displayed by the display device to an image of the object region acquired by the image acquisition device 58.

Figure 6:
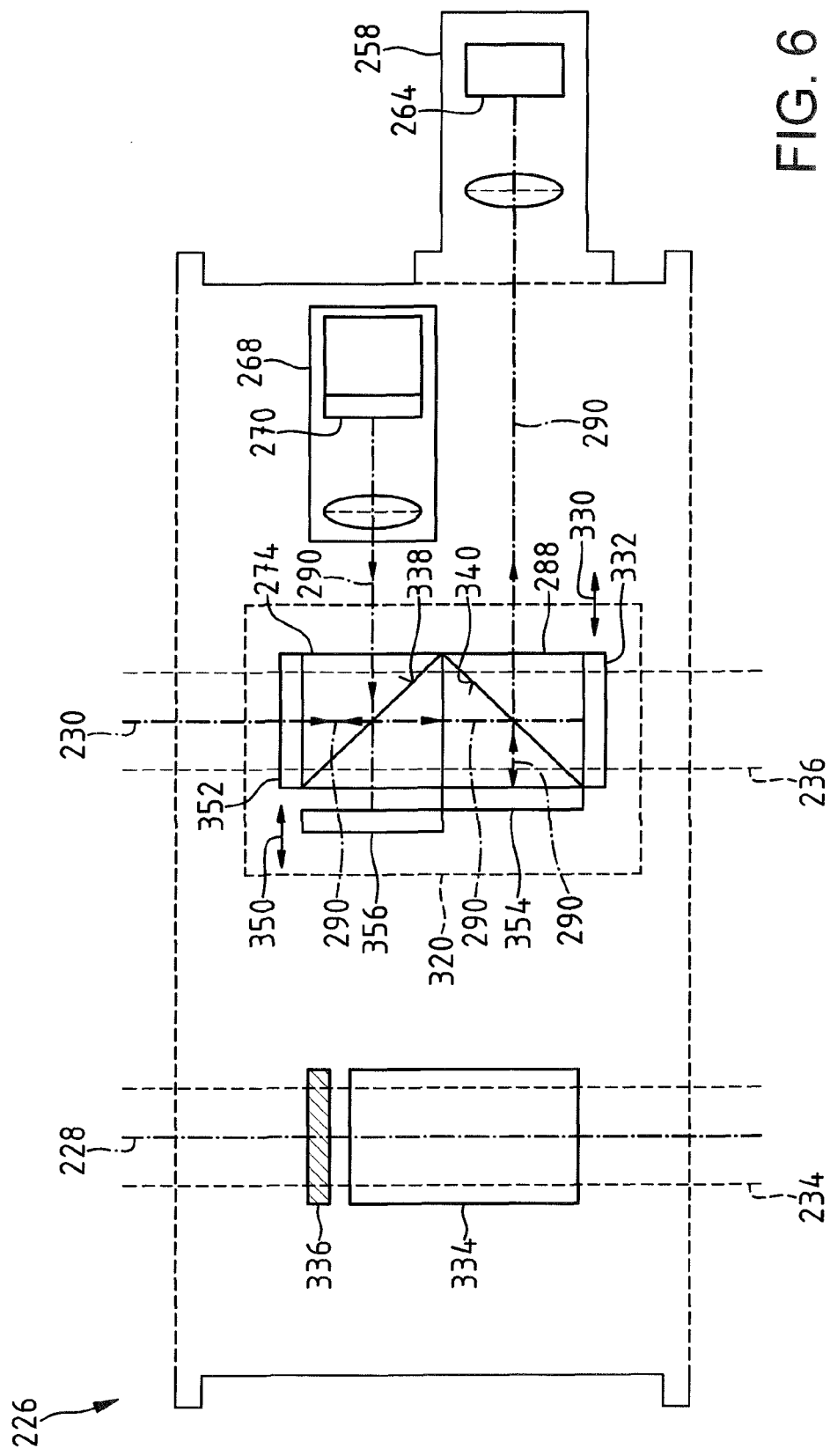
FIG. 6 shows a second module with an alternate configuration for mirroring data into a visualization apparatus.

FIG. 6 shows a second module 226 with an alternative design for mirroring data in a visualization apparatus, which second module corresponds functionally to the above described module 26. Insofar as the elements and assemblies shown in FIG. 6 are identical to the elements and assemblies depicted in the previous figures, in FIG. 6 the elements and assemblies have reference symbols in the form of numbers increased by the number 200 with respect to FIG. 2.

In order to optionally provide or suppress the optical beam path 290 from the display 270 of the display device 268 to the image sensor 264 of the image acquisition device 258 in the module 226, the module 226 contains a switchable device 320 comprising a beam deflection system, which has a mirror 352 which is relocatable corresponding to the double arrow 350. The mirror 352 is arranged on that side of the coupling-in beam splitter 274 through which the second stereoscopic component viewing beam path 230 passes. In the case of arrangement in the optical channel 236, the mirror 352 directs the light emitted by the display 270 of the display device 268 back into the coupling-in beam splitter 274, where it partially passes through the splitter surface 338 and passes with the beam path 290 into the coupling-out beam splitter 288. The light emitted by the display 270 of the display device 268 is in this case directed at the splitter surface 340 of the coupling-out beam splitter 288 to a further mirror 354. This further mirror 354 is arranged on that side of the coupling-out beam splitter 288 which faces away from the image acquisition device 258. With a beam path 290 which passes through the splitter surface 340 of the coupling-out beam splitter 288, this light emitted by the display 270 of the display device 268 is then guided through the coupling-out beam splitter 288 with a beam path 290 into the image acquisition device 258, which beam path passes through the splitter surface 340. If, on the other hand, the mirror 352 is arranged outside the optical channel 236, the image acquisition device 258 does not receive any light from the display 270 of the display device 268.

The beam deflection system of the device 320 contains a light trap 356, which swallows the light from the display device 268 passing through the splitter surface 338 of the coupling-in beam splitter 274 in order thus to suppress parasitic light which is damaging to the observation process in a surgical microscope.

Figure 7A:
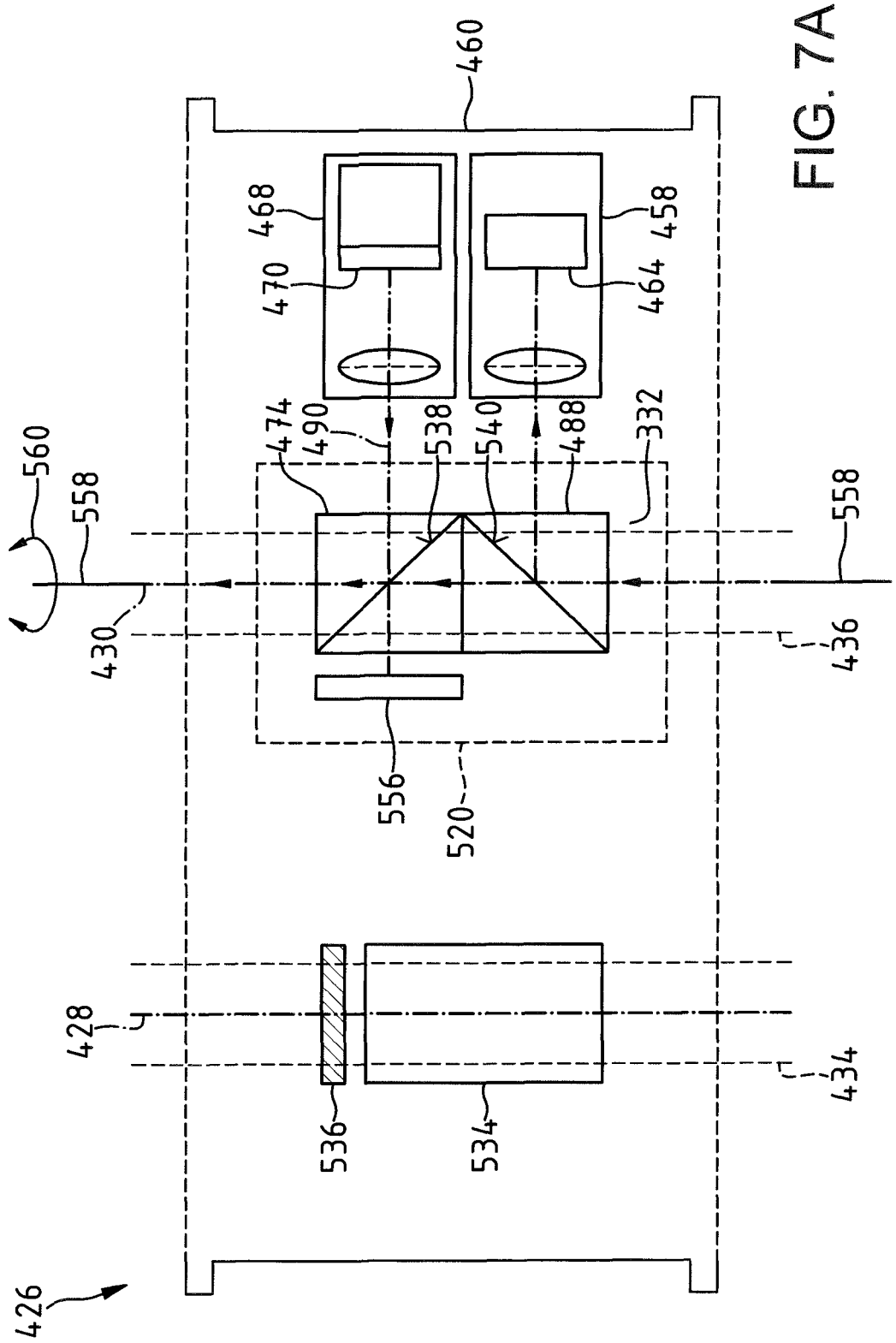
FIG. 7A shows a third module with an alternate embodiment for mirroring data into a visualization apparatus in a first setting.
Figure 7B:
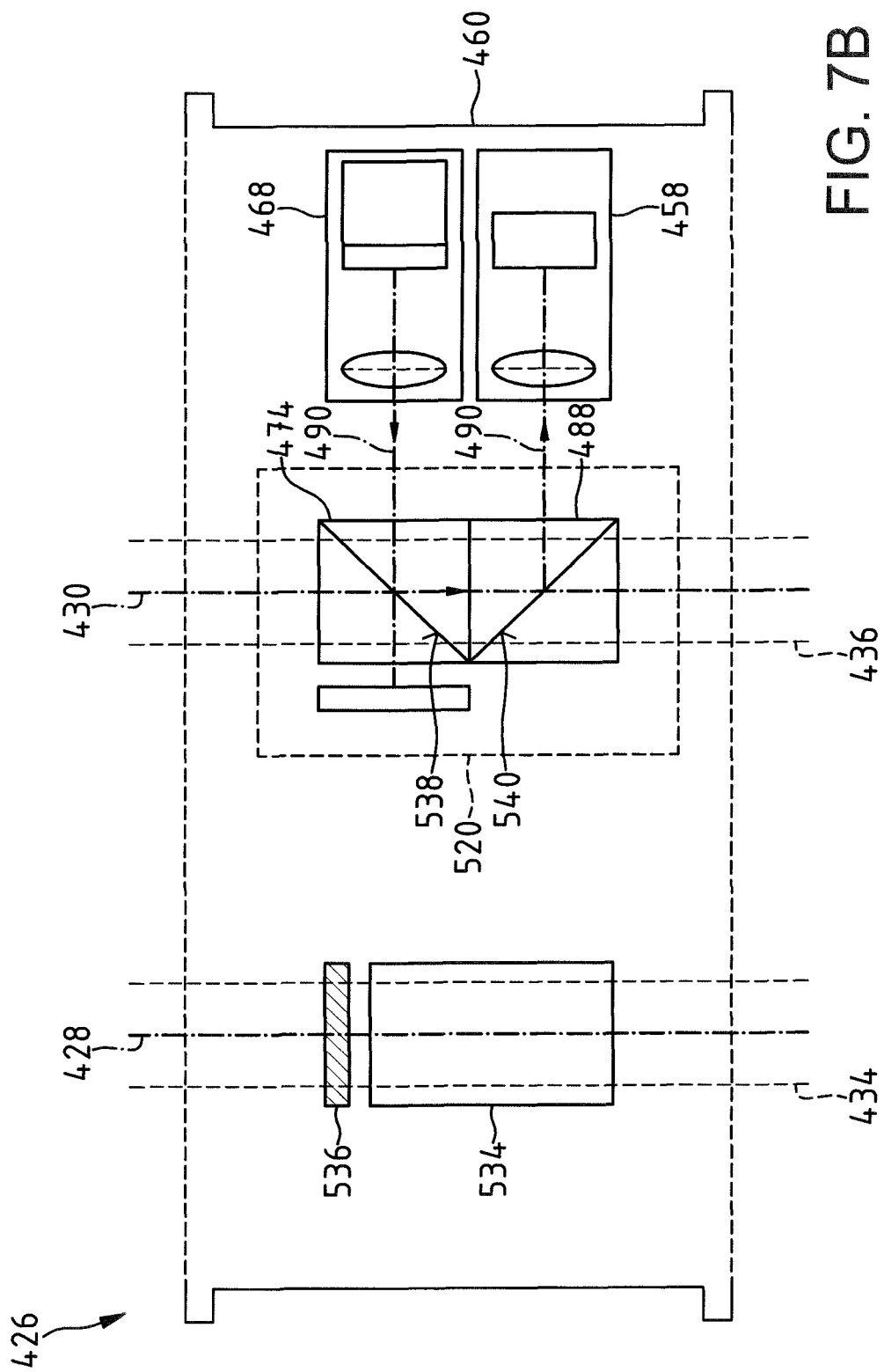
FIG. 7B shows the third module for mirroring data into a visualization apparatus in a second setting.

FIG. 7A and FIG. 7B show a third module 426 with an alternative design for mirroring data in a visualization apparatus, which third module corresponds functionally to the above described module 226. Insofar as the elements and assemblies shown in FIG. 7A and FIG. 7B are identical to the elements and assemblies shown in FIG. 6, the elements and assemblies have reference symbols in the form of numbers increased by the number 200 with respect to FIG. 6.

The image acquisition device 458 is integrated in the module basic body 460 in the module 426. In order to optionally provide or suppress the optical beam path 490 from the display 470 of the display device 468 to the image sensor 464 of the image acquisition device 458 in the module 426, the module 426 contains a switchable device 520 with a beam deflection system, in which the coupling-in beam splitter 474 and the coupling-out beam splitter 488 are mounted rotatably about the optical axis 558 of the optical channel 434 and can be moved, corresponding to the double arrow 560, out of a first position shown in FIG. 7A into the second position shown in FIG. 7B, and vice versa.

In the setting of the switchable device 520 shown in FIG. 7A, the image sensor 464 of the image acquisition device 458 does not receive any light from the display device 468. In contrast, in the setting of the switchable device 520 shown in FIG. 7B, a beam path 490 is supplied to the image sensor 464 of the image acquisition device 458 from the display device 468.

Figure 8A:
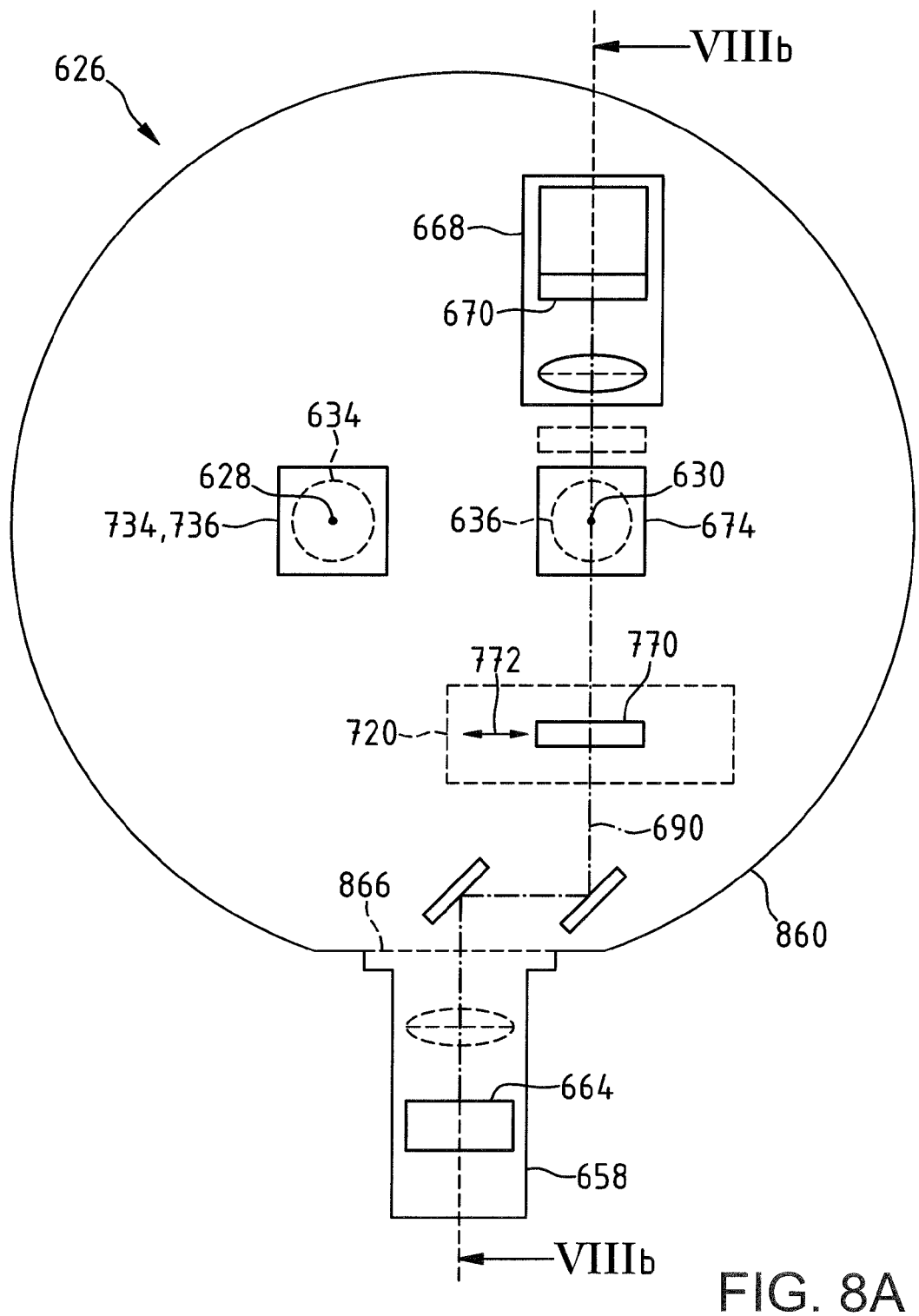
FIG. 8A shows a first view of a fourth module with an alternate configuration for mirroring data into a visualization apparatus.
Figure 8B:
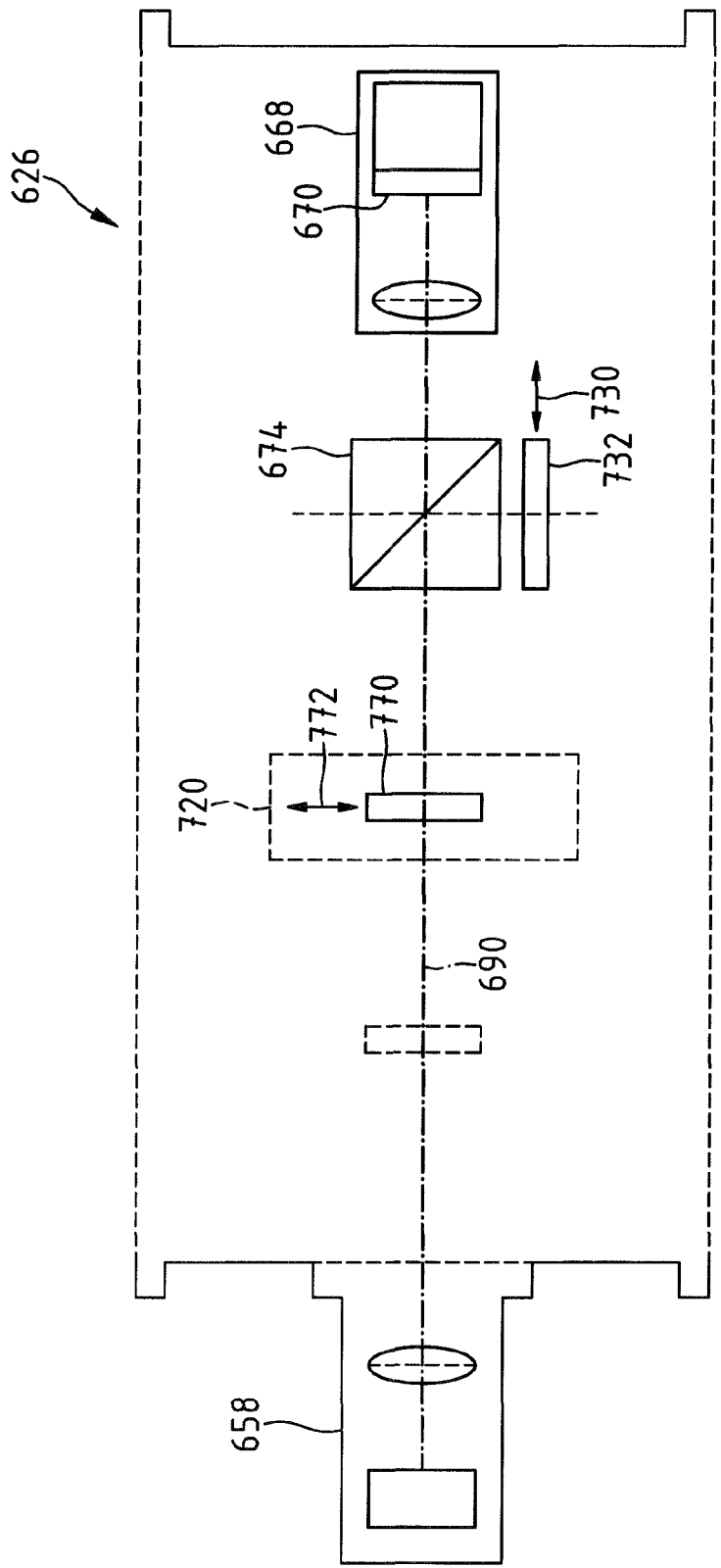
FIG. 8B shows a second view of the fourth module for mirroring data into a visualization apparatus.

FIG. 8A and FIG. 8B show a fourth module 626 with an alternative design for mirroring data in a visualization apparatus, which fourth module corresponds functionally to the above described module 226. Insofar as the elements and assemblies shown in FIG. 8A and FIG. 8B are identical to the elements and assemblies shown in FIG. 6, the elements and assemblies have reference symbols in the form of numbers which are increased by the number 400 with respect to FIG. 6.

FIG. 8A shows the module 626 as a section in a sectional plane which is perpendicular to the optical axes of the first optical channel 634 and of the further optical channel 636. FIG. 8B shows the module 626 as a perpendicular section along the line VIIIb-VIIIb from FIG. 8A.

In order to optionally provide or suppress the optical beam path 690 from the display 670 of the display device 668 to the image sensor 664 of the image acquisition device 658 in the module 626, the module 626 contains a beam splitter 674 and a switchable device 720 comprising a polarization filter 770, which can be arranged corresponding to the double arrow 772 in the beam path 690 supplied to the image acquisition device 658.

The beam splitter 674 is both a coupling-in beam splitter and a coupling-out beam splitter. In the module 626, the beam splitter 674 has a dual function, therefore.

It should be noted that even the accommodation of the polarization filter 770 in a pivot bearing for pivoting into and out of the beam path 690 can be provided for the polarization filter 770 instead of the linear relocatability in a linear guide.

If the polarization filter 770 is arranged in the beam path 690, the image sensor 664 does not receive any light from the display 670. If, on the other hand, the polarization filter 770 is positioned outside of the beam path 690, the image information displayed on the display 670 is supplied to the image sensor 664.

Figure 9A:
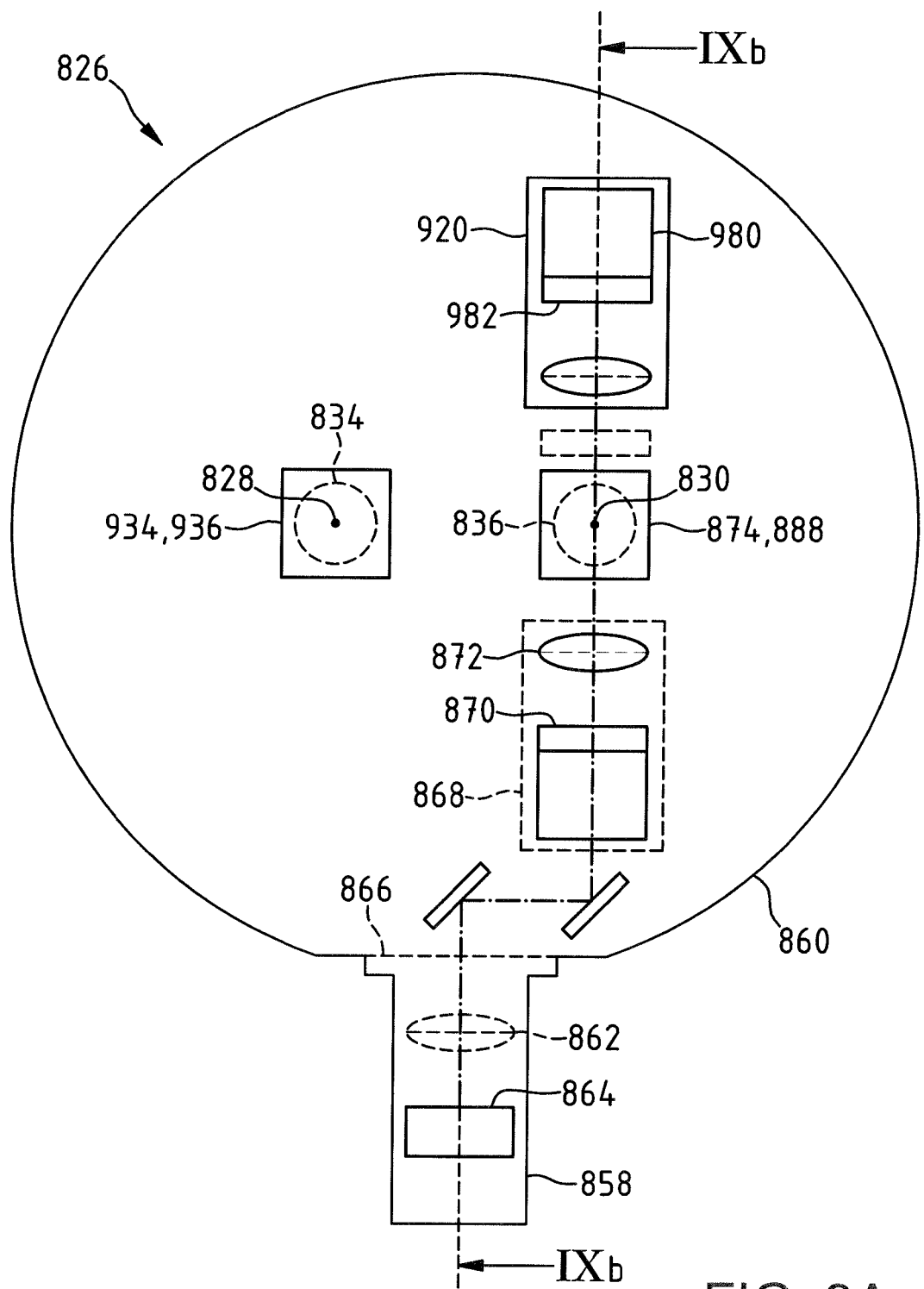
FIG. 9A shows a first view of a fifth module with an alternate configuration for mirroring data into a visualization apparatus.
Figure 9B:
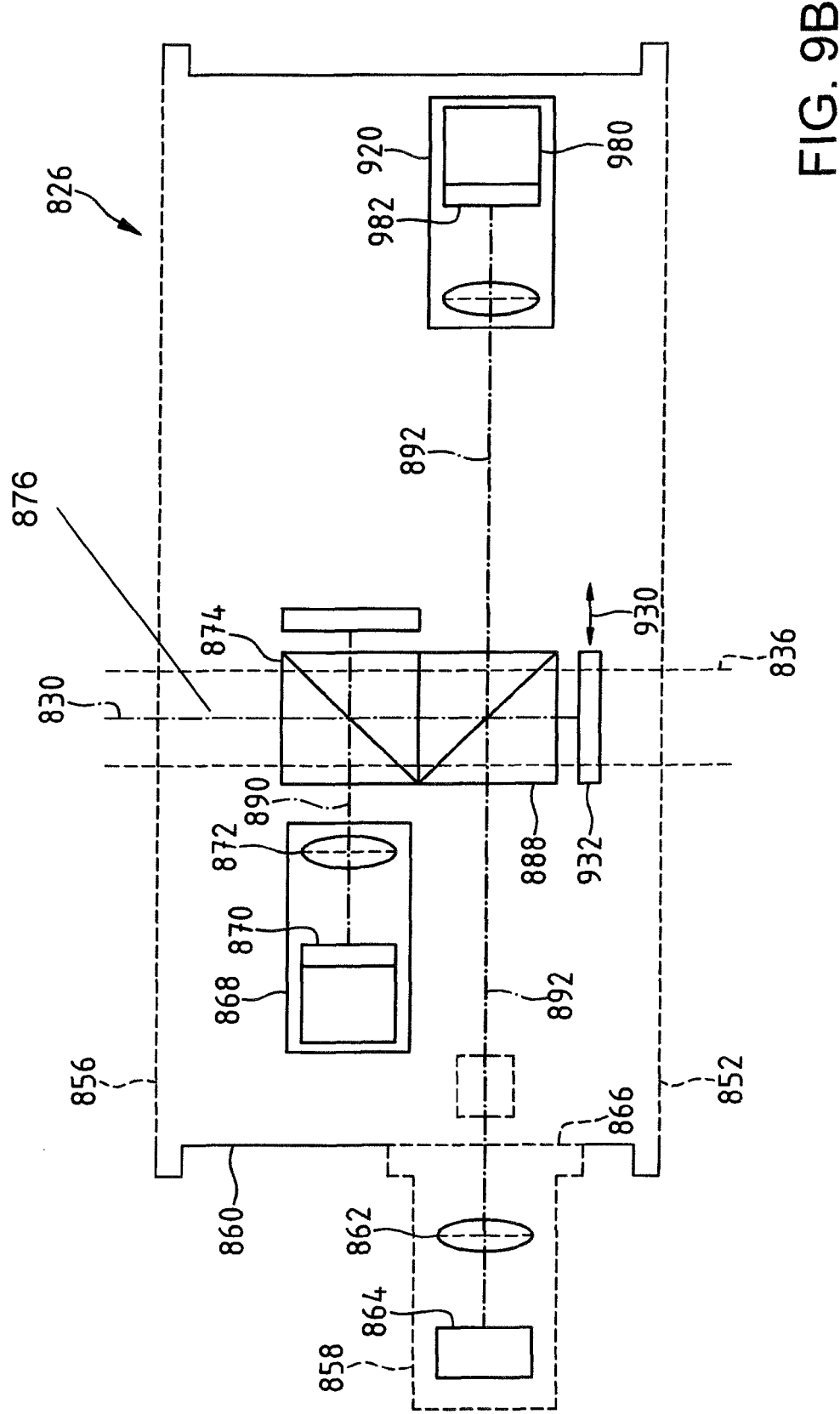
FIG. 9B shows a second view of the fifth module for mirroring data into a visualization apparatus; and, FIG. 9C shows a geometric structure which can be acquired by an image sensor and can be displayed in the module.

FIG. 9A and FIG. 9B show a further module 826 with an alternative design for mirroring data in a visualization apparatus. Insofar as the elements and assemblies shown in FIG. 9A and FIG. 9B are identical to the elements and assemblies shown in FIG. 6, the elements and assemblies have reference symbols in the form of numbers increased by the number 600 with respect to FIG. 6. In the module 826, the image displayed on a display 870 can be superimposed on the image of the object region 22 that can be perceived in the right-hand binocular viewer 20 of a binocular tube 860 in the second component viewing beam path 830 in the right-hand optical channel 836.

FIG. 9A shows the module 826 as a section in a sectional plane which is perpendicular to the optical axes of the first optical channel 836 and of the further optical channel 834. FIG. 9B shows the module 826 as a perpendicular section along the line VIIIb-VIIIb from FIG. 9A.

The module 826 has a first optical interface 852, at which it can be connected to a surgical microscope basic body by means of a dovetail coupling. The module 826 has a second optical interface 856 for the connection of a binocular tube 16 of a surgical microscope 10.

As image acquisition device 858, the module 826 contains an image acquisition device 858 connected to the module basic body 860 comprising an objective lens system 862 and an image sensor 864. There is an interface 866 at the module basic body 860 for fixing and releasing the image acquisition device 858.

It should be noted that the module 826 in a modified embodiment can in principle also contain an image acquisition device, which is fixedly integrated in the module basic body 860.

If the module 826 is integrated in a surgical microscope 10 corresponding to the module 226 described with reference to FIG. 1 to FIG. 5, the image acquisition device 858 receives the image of the object region 22 of the surgical microscope 10 via a coupling-out beam splitter 888 arranged in the module 826 in the right-hand optical channel 836. For this purpose, it is possible by means of the display device 868 in the module 826 to then display orientation information referenced with respect to the observation image of the object region 22 to an observer at the binocular viewer 20 of a surgical microscope 10. For this purpose, the display device 868 contains a display 870 and comprises an imaging lens system 872, by means of which the image information displayed on the display 870 is transferred into a parallel beam path 890 in order to direct the information into a binocular tube 16 via a coupling-in beam splitter 874 arranged in the module 826 with an optical display beam path 876 superimposed on the stereoscopic component viewing beam path 830.

Figure 9C:
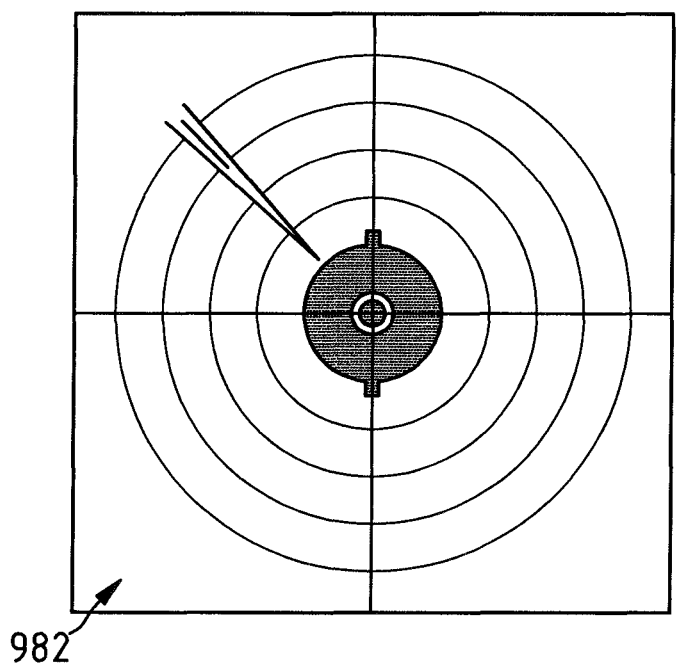

In the module 826, there is a switchable device 920 for optionally providing and suppressing an image of a geometric structure 982 on the image sensor 864 of the image acquisition device 858. For this purpose, the switchable device 920 contains an illumination unit 980, on which the geometric structure 982 is arranged. By way of example, FIG. 9C shows a possible geometric structure 982 as a plan view. The geometric structure 982 is positioned spaced apart from the display 870 and fixed in location relative to the module basic body 860. In the case of illumination of the geometric structure 982, that is, in a first switching state of the device 920, the image of the geometric structure 982 with an optical beam path 892 passing through the coupling-out beam splitter 888 is provided on the image sensor 864.

If, on the other hand, in a further switching state of the device 920, which is different than the first switching state, the geometric structure 982 is not illuminated, there is no optical beam path from the geometric structure 982 to the image sensor 864 in the module 826. An optical beam path 892 from the geometric structure 982 to the image sensor 864 is then suppressed in the absence of light beams originating from the geometric structure 982.

By virtue of the image of the geometric structure acquired by the image acquisition device 858 being subjected to image analysis using a computer program, as described above, the display device 868 can also in this case be matched to the image acquisition device 858 in the module 826.

By way of summary, in particular, the following details should be retained: the invention relates to a module (26, 226, 426, 626) for a visualization apparatus comprising an imaging optical unit accommodated in a basic body 12 for generating an observation image of an object region 22 with an optical viewing beam path (30, 230, 430, 630). The module comprises a display device (68, 268, 468, 668) for visualizing an image superimposed on the observation image of the object region 22 with orientation information comprising a display (70, 270, 470, 670). The module has an image acquisition device (58, 258, 458, 658) comprising an image sensor (64, 264, 464, 664) for acquiring an image of the object region 22. The module contains a switchable device (120, 320, 520, 720) for optionally providing and suppressing an optical beam path (90, 290, 490, 690) from the display to the image sensor (64, 264, 464, 664), which switchable device, in a first switching state, provides the image of a geometric structure 92 displayed on the display (70, 270, 670) on the image sensor (64, 264, 464, 664) with an optical beam path (90, 290, 490, 690) and, in a further switching state, which is different than the first switching state, suppresses the optical beam path (90, 290, 490, 690) from a geometric structure 92 displayed on the display (70, 270, 470, 670) to the image sensor (64, 264, 464, 664).

It is understood that the foregoing description is that of the preferred embodiments of the invention and that various changes and modifications may be made thereto without departing from the spirit and scope of the invention as defined in the appended claims.

LIST OF REFERENCE SYMBOLS

10 Surgical microscope
12 Basic body
14 Supporting arm
16 Binocular tube
18, 20 Binocular viewer
22 Object region
24 Eye
26 Module
28, 30 Component viewing beam path
32 Microscope main objective
34, 36 Optical channel
38 Magnification system
40, 42 Tube lenses
44, 46 Intermediate image plane
48, 50 Ocular lens system
52, 56 Optomechanical interface
58 Image acquisition device
60 Module basic body
62 Objective lens system
64 Image sensor 66 Interface
68 Display device
70 Display
72 Imaging lens system
74 Coupling-in beam splitter
76 Display beam path
78 Image
80, 82 Orientation information
84 Arrow
86 Angle
88 Coupling-out beam splitter
90 Beam path
91 Image to be observed
92 Structure
93 Image sensor field of view
94 Center
95 Display field of view
96 Circular disk
98 Circular ring
100, 102 Marking
104, 106 Lines
108, 110, 112, 114 Circular lines
116 Azimuthal angle marking
118a, 118b, 118c Angle line marks
120 Device
122 Prism
124 Shutter
126, 128 Mirror surface
130 Double arrow
132 Optical element
134 Glass cube
136 Gray filter
138, 140 Splitter surface
226 Module
228, 230 Component viewing beam path
234, 236 Optical channel
258 Image acquisition device
264 Image sensor
268 Display device
270 Display
274 Coupling-in beam splitter
288 Coupling-out beam splitter
290 Beam path
292 Device
320 Device
330 Double arrow
332 Optical element
334 Glass cube
336 Gray filter
338, 340 Splitter surface
350 Double arrow
352, 354 Mirror
356 Light trap
426 Module
428, 430 Component viewing beam path
434, 436 Optical channel
458 Image acquisition device
460 Basic body
464 Image sensor
468 Display device
470 Display
474 Coupling-in beam splitter
488 Coupling-out beam splitter
490 Beam path
520 Device
534 Glass cube
536 Gray filter
538, 540 Splitter surface
558 Optical axis
560 Double arrow
626 Module
628, 630 Component viewing beam path
634, 636 Optical channel
658 Image acquisition device
664 Image sensor
668 Display device
670 Display
674 Beam splitter (coupling-in beam splitter and coupling-out beam splitter)
690 Beam path
720 Device
770 Polarization filter
772 Double arrow
816 Binocular tube
826 Module
828, 830 Component viewing beam path
834, 836 Optical channel
852, 856 Optical interface
858 Image acquisition device
860 Basic body
862 Objective lens system
864 Image sensor
866 Interface
868 Display device
870 Display
872 Imaging lens system
874 Coupling-in beam splitter
876 Optical display beam path
888 Coupling-out beam splitter
890, 892 Beam path
920 Device
980 Illumination unit
982 Structure

What is claimed is:

1. A module for a visualization apparatus for viewing an object, the visualization apparatus having a base body and an imaging optic defining an optical viewing beam path and being accommodated in said base body; said imaging optic being configured for generating a viewing image of a region of the object with said optical viewing beam path; the module comprising:

a display unit having a display and being configured for visualizing an image superposed on said viewing image of said object region;

said superposed image having orientation information in said optical viewing beam path;

an optical channel for said optical viewing beam path;

an image acquisition unit having an image sensor for detecting an image of the region of the object;

an in-coupling beam splitter arranged in said optical channel;

said display and said image sensor conjointly defining an optical beam path running from said display to said image sensor and passing through said beam splitter;

a switching unit for selectively passing and blocking said optical beam path;

said in-coupling beam splitter being configured to deflect said optical beam path from said display into said optical channel so as to be superposed on said optical viewing beam path;

said switching unit having a first switching state wherein an image of a geometric structure shown on said display is made available on said image sensor via said optical beam path and having a second switching state, which is different from said first switching state, wherein said optical beam path is blocked to prevent said geometric structure shown on said display from reaching said image sensor;

an out-coupling beam splitter arranged in said optical channel for said optical viewing beam path;

said out-coupling beam splitter being configured to conduct said viewing image of said object region to said image acquisition unit;

said switching unit including a beam deflection system configured to deflect said optical beam path coming from said display and passing through said in-coupling beam splitter and then being conducted to said image sensor via said out-coupling beam splitter;

said in-coupling beam splitter having a side facing away from said display and said out-coupling beam splitter having a side facing away from said image acquisition unit;

said beam deflection system including a first mirror surface and a second mirror surface; and, said beam deflection system being configured to guide said optical beam path coming from said display at said side of said in-coupling beam splitter via reflection onto said first mirror surface and then to said second mirror surface which, in turn, reflects said optical beam path to said side of said out-coupling beam splitter.

2. The module of claim 1, wherein said beam deflection system is configured as a 90° prism.

3. The module of claim 1, further comprising an optical element arranged between said in-coupling beam splitter and said beam deflection system; and, said optical element being configured for selectively passing and interrupting said optical beam path passing through said in-coupling beam splitter.

4. The module of claim 1, wherein said optical channel is an optical channel for a first stereoscopic component viewing beam path, and a further optical channel for a second stereoscopic component viewing beam path is provided, which further optical channel contains an optical element for the at least partial compensation of the optical path length for the first stereoscopic component viewing beam path in the optical channel and the optical path length for the second stereoscopic component viewing beam path in the further optical channel.

5. The module of claim 1, wherein the optical channel is an optical channel for a first stereoscopic component viewing beam path, wherein, in addition, a further optical channel for a second stereoscopic component viewing beam path is provided, which contains an optical element for the at least partial compensation of the light intensity of the first stereoscopic component viewing beam path in the optical channel and the light intensity of the second stereoscopic component viewing beam path in the further optical channel.

6. The module of claim 1, further comprising an optical element arranged in the optical viewing beam path on that side of the out-coupling beam splitter which faces toward the object region for selectively enabling and interrupting the optical viewing beam path supplied to the out-coupling beam splitter from the object region.

7. The module of claim 1, wherein the geometric structure comprises a pattern defining the position and at least one length and the azimuthal orientation.

8. The module of claim 3, wherein said optical element is configured as a shutter mounted so as to be movable into and out of said optical beam path.

9. The module of claim 8, wherein said shutter is configured as a displaceable light trap.

10. A module for a visualization apparatus for viewing an object, the visualization apparatus having a base body and an imaging optic defining an optical viewing beam path and being accommodated in said base body; said imaging optic being configured for generating a viewing image of a region of the object with said optical viewing beam path; the module comprising:

a display unit having a display and being configured for visualizing an image superposed on said viewing image of said object region;

said superposed image having orientation information in said optical viewing beam path;

an optical channel for said optical viewing beam path;

an image acquisition unit having an image sensor for detecting an image of the region of the object;

an in-coupling beam splitter arranged in said optical channel;

said display and said image sensor conjointly defining an optical beam path running from said display to said image sensor and passing through said beam splitter;

a switching unit for selectively passing and blocking said optical beam path;

said in-coupling beam splitter being configured to deflect said optical beam path from said display into said optical channel so as to be superposed on said optical viewing beam path;

said switching unit having a first switching state wherein an image of a geometric structure shown on said display is made available on said image sensor via said optical beam path and having a second switching state, which is different from said first switching state, wherein said optical beam path is blocked to prevent said geometric structure shown on said display from reaching said image sensor;

an out-coupling beam splitter arranged in said optical channel for said optical viewing beam path;

said out-coupling beam splitter being configured to conduct said viewing image of said object region to said image acquisition unit;

said in-coupling beam splitter and said out-coupling beam splitter having respective splitter surfaces; and, said switching unit including a beam deflecting system having a displaceable mirror, which reflects said optical beam path from said display superposed on said optical viewing beam path via said in-coupling beam splitter by deflection on said splitter surface thereof back into said in-coupling beam splitter and directs said optical beam path through the splitter surface of said in-coupling beam splitter to the out-coupling beam splitter, in which said optical beam path is reflected on the splitter surface thereof to a further mirror, which is arranged on a side of the out-coupling beam splitter which faces away from the image acquisition unit, which further mirror directs the optical beam path through the out-coupling beam splitter along a beam path which passes through the splitter surface to the image acquisition unit.

11. A module for a visualization apparatus for viewing an object, the visualization apparatus having a base body and an imaging optic defining an optical viewing beam path and being accommodated in said base body; said imaging optic being configured for generating a viewing image of a region of the object with said optical viewing beam path; the module comprising:

a display unit having a display and being configured for visualizing an image superposed on said viewing image of said object region;

said superposed image having orientation information in said optical viewing beam path;

an optical channel for said optical viewing beam path;

an image acquisition unit having an image sensor for detecting an image of the region of the object;

an in-coupling beam splitter arranged in said optical channel;

said display and said image sensor conjointly defining an optical beam path running from said display to said image sensor and passing through said beam splitter;

a switching unit for selectively passing and blocking said optical beam path;

said in-coupling beam splitter being configured to deflect said optical beam path from said display into said optical channel so as to be superposed on said optical viewing beam path;

said switching unit having a first switching state wherein an image of a geometric structure shown on said display is made available on said image sensor via said optical beam path and having a second switching state, which is different from said first switching state, wherein said optical beam path is blocked to prevent said geometric structure shown on said display from reaching said image sensor;

an out-coupling beam splitter arranged in said optical channel for said optical viewing beam path;

said out-coupling beam splitter being configured to conduct said viewing image of said object region to said image acquisition unit; and, a displacing unit as a switchable device for selectively providing and blocking said optical beam path from said display to said image sensor in order to move said in-coupling beam splitter and said out-coupling beam splitter from a first position into a second position, and vice versa, wherein said out-coupling beam splitter in the first position directs the viewing image of said object region to said image acquisition unit and said in-coupling beam splitter superimposes an image displayed on the display of said display unit on the viewing image of said object region in the viewing beam path, and wherein the in-coupling beam splitter in said second position directs an image displayed on said display of said display unit to said out-coupling beam splitter, which, in said second position, directs said image to the image acquisition unit.

12. A module for a visualization apparatus for viewing an object, the visualization apparatus having a base body and an imaging optic defining an optical viewing beam path and being accommodated in said base body; said imaging optic being configured for generating a viewing image of a region of the object with said optical viewing beam path; the module comprising:

a display unit having a display and being configured for visualizing an image superposed on said viewing image of said object region;

said superposed image having orientation information in said optical viewing beam path;

an optical channel for said optical viewing beam path;

an image acquisition unit having an image sensor for detecting an image of the region of the object;

a multifunction beam splitter arranged in said optical channel;

said display and said image sensor conjointly defining an optical beam path running from said display to said image sensor and passing through said beam splitter;

a switching unit for selectively passing and blocking said optical beam path;

said multifunction beam splitter being configured to deflect and couple in said optical beam path from said display into said optical channel so as to be superposed on said optical viewing beam path;

said switching unit having a first switching state wherein an image of a geometric structure shown on said display is made available on said image sensor via said optical beam path and having a second switching state, which is different from said first switching state, wherein said optical beam path is blocked to prevent said geometric structure shown on said display from reaching said image sensor;

said multifunction beam splitter being further arranged in said optical channel for said optical viewing beam path to couple out and conduct said viewing image of said object region to said image acquisition unit;

said display unit for visualizing an image superimposed on the viewing image of the object region is formed with polarized light;

a switchable optical element being arranged between said multifunction beam splitter and the image sensor; and, said switchable optical element, in a first switching state, being transmissive to the polarized light of said display unit which passes through said multifunction beam splitter to said image sensor of said image acquisition unit and, in a second switching state, which is different than the first switching state, blocking the passage of the polarized light from said display unit to said image sensor.

13. A module for a visualization apparatus for viewing an object, the visualization apparatus having a base body and an imaging optic defining an optical viewing beam path and being accommodated in said base body; said imaging optic being configured for generating a viewing image of a region of the object with said optical viewing beam path; the module comprising:

a display unit having a display and being configured for visualizing an image superposed on said viewing image of said object region;

said superposed image having orientation information in said optical viewing beam path;

an optical channel for said optical viewing beam path;

an image acquisition unit having an image sensor for detecting an image of the region of the object;

a geometric structure spaced from said display and arranged fixed in position relative to said base body;

a switching unit for selectively providing and blocking an image of said geometric structure on said image sensor;

a multifunction beam splitter arranged in said optical channel so as to permit said optical viewing beam path to pass therethrough;

said switching unit having a first switching state wherein said image of said geometric structure is directed onto said image sensor via an optical beam path which passes through said multifunction beam splitter;

said multifunction beam splitter being configured to couple out and conduct said viewing image of said object region to said image acquisition unit and to couple said optical beam path and said geometric structure into said optical channel; and, said switching unit having a second switching state, which is different from said first switching state, wherein said optical beam path is blocked from said geometric structure to said image sensor.

14. The module of claim 13, further comprising an in-coupling beam splitter arranged in said optical channel; and, said in-coupling beam splitter being configured to superpose an image displayed on said display of said display unit onto said viewing image of said object region in said viewing beam path.

15. The module of claim 13, further comprising an illumination unit for illuminating said geometric structure; and, said illumination unit defining said switching unit for selectively providing and blocking said image of said geometric structure on said image sensor.

16. The module of claim 14, wherein said optical channel is an optical channel for a first stereoscopic component viewing beam path, and a further optical channel for a second stereoscopic component viewing beam path is provided, which further optical channel contains an optical element for the at least partial compensation of the optical path length for the first stereoscopic component viewing beam path in the optical channel and the optical path length for the second stereoscopic component viewing beam path in the further optical channel.

17. The module of claim 14, wherein the optical channel is an optical channel for a first stereoscopic component viewing beam path, wherein, in addition, a further optical channel for a second stereoscopic component viewing beam path is provided, which contain an optical element for the at least partial compensation of the light intensity of the first stereoscopic component viewing beam path in the optical channel and the light intensity of the second stereoscopic component viewing beam path in the further optical channel.

18. The module of claim 13, further comprising an optical element arranged in the optical viewing beam path on that side of the multifunction beam splitter which faces toward the object region for selectively enabling and interrupting the optical viewing beam path supplied to the multifunction beam splitter from the object region.

19. The module of claim 13, wherein the geometric structure comprises a pattern defining the position and at least one length and the azimuthal orientation.

20. A visualization apparatus for viewing an object, the visualization apparatus comprising:
a base body;
an imaging optic mounted in said base body and defining an optical viewing beam path;
said imaging optic being configured for generating a viewing image of a region of the object via said optical viewing beam path;
a module including:
a display unit having a display and being configured for visualizing an image superposed on said viewing image of said object region;
said superposed image having orientation information in said optical viewing beam path;
an optical channel for said optical viewing beam path;
an image acquisition unit having an image sensor for detecting an image of the region of the object;
an in-coupling beam splitter arranged in said optical channel;
said display and said image sensor conjointly defining an optical beam path running from said display to said image sensor and passing through said beam splitter;
a switching unit for selectively passing and blocking said optical beam path;
said in-coupling beam splitter being configured to deflect said optical beam path from said display into said optical channel so as to be superposed on said optical viewing beam path;
said switching unit having a first switching state wherein an image of a geometric structure shown on said display is made available on said image sensor via said optical beam path and having a second switching state, which is different from said first switching state, wherein said optical beam path is blocked to prevent said geometric structure shown on said display from reaching said image sensor;
an out-coupling beam splitter arranged in said optical channel for said optical viewing beam path;
said out-coupling beam splitter being configured to conduct said viewing image of said object region to said image acquisition unit;
said switching unit including a beam deflection system configured to deflect said optical beam path coming from said display and passing through said in-coupling beam splitter and then being conducted to said image sensor via said out-coupling beam splitter;
said in-coupling beam splitter having a side facing away from said display and said out-coupling beam splitter having a side facing away from said image acquisition unit;
said beam deflection system including a first mirror surface and a second mirror surface; and,
said beam deflection system being configured to guide said optical beam path coming from said display at said side of said in-coupling beam splitter via reflection onto said first mirror surface and then to said second mirror surface which, in turn, reflects said optical beam path to said side of said out-coupling beam splitter.

21. The visualization apparatus of claim 20, wherein said visualization apparatus is a surgical microscope.

22. The visualization apparatus of claim 20, further comprising:
a computer connected to said image acquisition unit and said display unit;
said computer incorporating a computer program for carrying out the following method steps:
providing said image of said geometric structure to said image acquisition unit;
determining correction parameters from the position and/or the size and/or the orientation of the geometric structure in the image of the geometric structure acquired by the image acquisition unit on the image sensor; and,
compensating for in particular a discrepancy, brought about by tolerances of assemblies, in the position and/or the orientation and/or the scaling of an image acquired in the image acquisition unit on the image sensor in a system of coordinates which is fixed with respect to the display of the display unit for the data which can be displayed by the display unit.

23. A method for adapting data displayed by a display unit in a visualization apparatus which includes: a base body; an imaging optic mounted in said base body and defining an optical viewing beam path; said imaging optic being configured for generating a viewing image of a region of the object with said optical viewing beam path; a module including: said display unit having a display and being configured for visualizing an image superposed on said viewing image of said object region; said superposed image having orientation information in said optical viewing beam path; an optical channel for said optical viewing beam path; an image acquisition unit having an image sensor for detecting an image of the region of the object; an in-coupling beam splitter arranged in said optical channel; said display and said image sensor conjointly defining an optical beam path running from said display to said image sensor and passing through said beam splitter; a switching unit for selectively passing and blocking said optical beam path; said in-coupling beam splitter being configured to deflect said optical beam path from said display into said optical channel so as to be superposed on said optical viewing beam path; and, said switching unit having a first switching state wherein an image of a geometric structure shown on said display is made available on said image sensor via said optical beam path and having a second switching state, which is different from said first switching state, wherein said optical beam path is blocked to prevent said geometric structure shown on said display from reaching said image sensor; an out-coupling beam splitter arranged in said optical channel for said optical viewing beam path; said out-coupling beam splitter being configured to conduct said viewing image of said object region to said image acquisition unit; said switching unit including a beam deflection system configured to deflect said optical beam path coming from said display and passing through said in-coupling beam splitter and then being conducted to said image sensor via said out-coupling beam splitter; said in-coupling beam splitter having a side facing away from said display and said out-coupling beam splitter having a side facing away from said image acquisition unit; said beam deflection system including a first mirror surface and a second mirror surface; and, said beam deflection system being configured to guide said optical beam path coming from said display at said side of said in-coupling beam splitter via reflection onto said first mirror surface and then to said second mirror surface which, in turn, reflects said optical beam path to said side of said out-coupling beam splitter; the method being for adapting said data to the image of the object region acquired by said image acquisition unit and comprising the steps of:

provide said image of said geometric structure to said image acquisition unit;

determining correction parameters from the position and/or the size and/or the orientation of the geometric structure in the image of the geometric structure acquired by the image acquisition unit on the image sensor; and, compensating for in particular a discrepancy, brought about by tolerances of assemblies, in the position and/or the orientation and/or the scaling of an image acquired in the image acquisition unit on the image sensor in a system of coordinates which is fixed with respect to the display of the display unit for the data which can be displayed by the display unit.

* * * * *